United States Patent

Damren et al.

(10) Patent No.: US 9,891,080 B2
(45) Date of Patent: Feb. 13, 2018

(54) PROBE ASSEMBLY

(71) Applicant: GE HEALTHCARE BIO-SCIENCES CORP., Piscataway, NJ (US)

(72) Inventors: Richard L. Damren, Marlborough, MA (US); Colin R. Tuohey, Medway, MA (US); Thomas Erdenberger, Arlington, MA (US); Michael Fisher, Ashland, MA (US); Jonathan A. Kenney, Lakeville, MA (US); Parrish M. Galliher, Littleton, MA (US); Joseph D. Crowell, South Hamilton, MA (US)

(73) Assignee: GE HEALTHCARE BIO-SCIENCES CORP., Marlborough, MA (US)

( * ) Notice: Subject to any disclaimer, the term of this patent is extended or adjusted under 35 U.S.C. 154(b) by 770 days.

(21) Appl. No.: 14/353,344

(22) PCT Filed: Oct. 28, 2012

(86) PCT No.: PCT/US2012/062345
§ 371 (c)(1),
(2) Date: Apr. 22, 2014

(87) PCT Pub. No.: WO2013/063550
PCT Pub. Date: May 2, 2013

(65) Prior Publication Data
US 2014/0260712 A1    Sep. 18, 2014

Related U.S. Application Data

(60) Provisional application No. 61/552,974, filed on Oct. 28, 2011.

(51) Int. Cl.
*G01D 11/24* (2006.01)
*A61M 39/18* (2006.01)

(52) U.S. Cl.
CPC .............. *G01D 11/24* (2013.01); *A61M 39/18* (2013.01)

(58) Field of Classification Search
CPC .............................. A61M 39/18; G01D 11/18
(Continued)

(56) References Cited

U.S. PATENT DOCUMENTS 3,983,756 A * 10/1976 Danguillier .............. G01K 1/14
137/317
4,096,754 A *  6/1978 Beveridge, Jr. ..... G01L 19/0007
137/317
(Continued)

FOREIGN PATENT DOCUMENTS

CN    1897908 A    1/2007
EP    0311787 A2   4/1989
(Continued)

OTHER PUBLICATIONS

European Search Report dated Aug. 5, 2015 for European Application No. 12843257.2.
(Continued)

*Primary Examiner* — Daniel S Larkin
(74) *Attorney, Agent, or Firm* — Grogan, Tuccillo & Vanderleeden, LLP

(57) ABSTRACT

A probe assembly for inserting a probe into a flexible or semi-rigid vessel or tubing having a distal aseptic connector for coupling to the vessel or tubing, the probe sheath comprising at least a portion that is rigid, the probe sheath extending longitudinally from the aseptic connector and having at least one inner longitudinal lumen configured to receive an elongate sensor or probe body and to permit longitudinal movement of the sensor/probe body within the probe sheath lumen, and an actuator for deploying a probe within the vessel or tubing by advancing the probe body
(Continued)

through the aseptic connector to a position where the probe can measure at least one parameter within the vessel or tubing is disclosed herein.

13 Claims, 7 Drawing Sheets

(58) Field of Classification Search
USPC .......................................................... 73/866.5
See application file for complete search history.

(56) References Cited

U.S. PATENT DOCUMENTS

| | | | |
|---|---|---|---|
| 5,174,325 A * | 12/1992 | Okel | G01K 1/146 137/317 |
| 5,279,583 A | 1/1994 | Shober, Jr. et al. | |
| 7,272,983 B2 * | 9/2007 | Caderas | F15B 15/261 73/866.5 |
| 2002/0093192 A1 | 7/2002 | Matkovich | |
| 2004/0199139 A1 | 10/2004 | Fowles | |
| 2005/0165328 A1 | 7/2005 | Heske et al. | |
| 2005/0177025 A1 | 8/2005 | Jaker et al. | |
| 2005/0211373 A1 | 9/2005 | Tomasetti et al. | |
| 2005/0239199 A1 | 10/2005 | Kunas et al. | |
| 2009/0151482 A1 * | 6/2009 | Klees | G01D 21/00 73/866.5 |
| 2010/0109882 A1 * | 5/2010 | Lohmann | G01N 27/286 340/584 |
| 2010/0149907 A1 | 6/2010 | Watkins et al. | |
| 2011/0124035 A1 | 5/2011 | Broadley et al. | |

FOREIGN PATENT DOCUMENTS

| | | |
|---|---|---|
| JP | 2002-510996 A | 4/2002 |
| JP | 2002-514941 A | 5/2002 |
| JP | 2003-169663 A | 6/2003 |
| JP | 2003-289851 A | 10/2003 |
| JP | 2007-534335 A | 11/2007 |
| JP | 2007534335 A | 11/2007 |
| JP | 2010-509984 A | 4/2010 |

OTHER PUBLICATIONS

Japanese Office Action dated Apr. 4, 2017 for Patent Application No. 2014-539100.

* cited by examiner

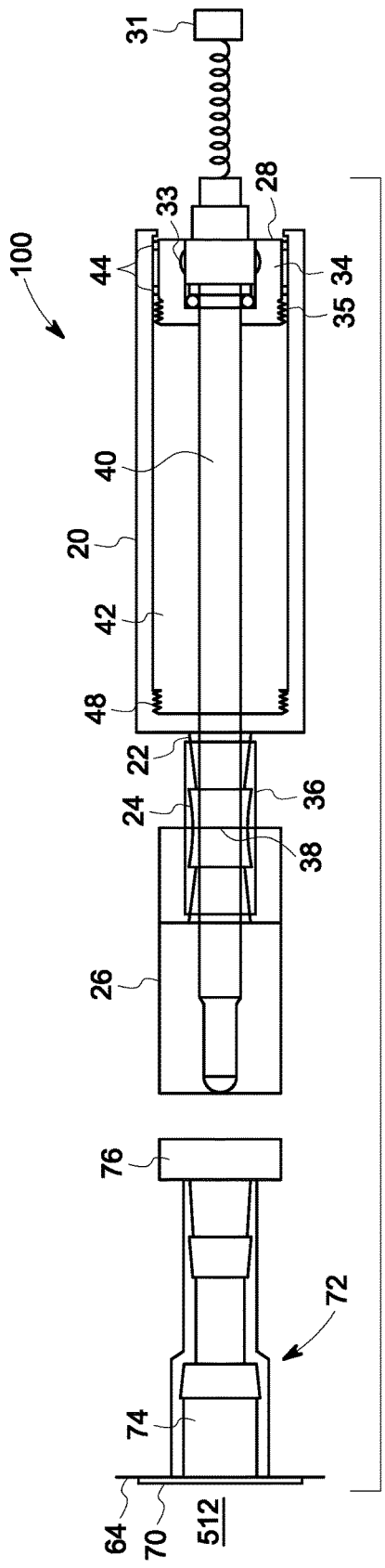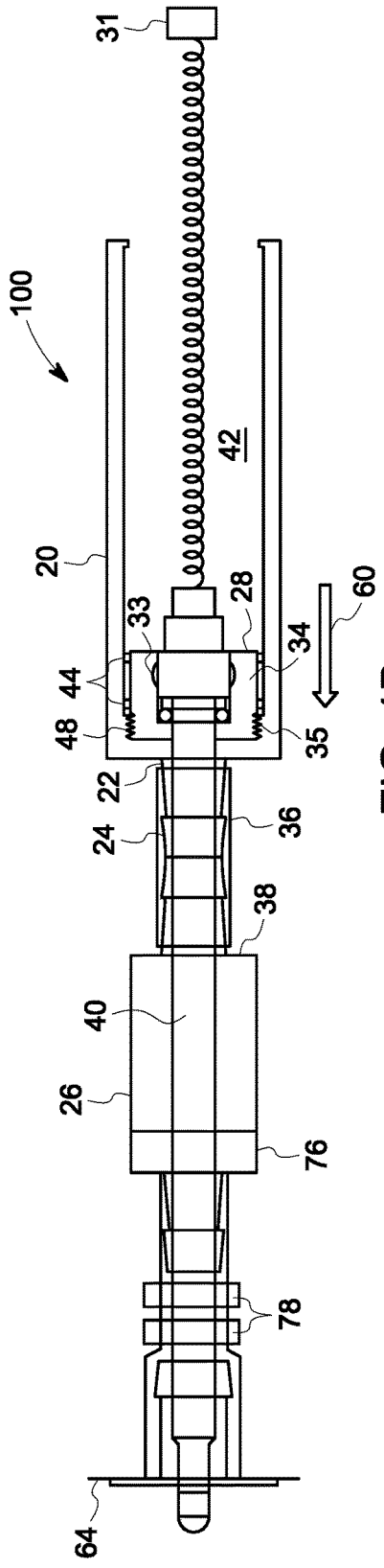
FIG. 1A
FIG. 1B

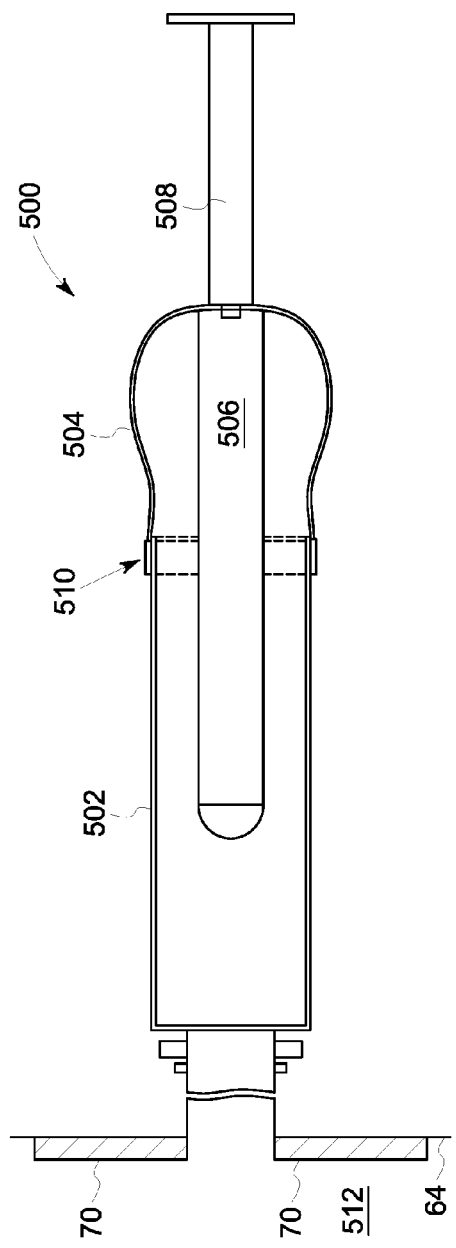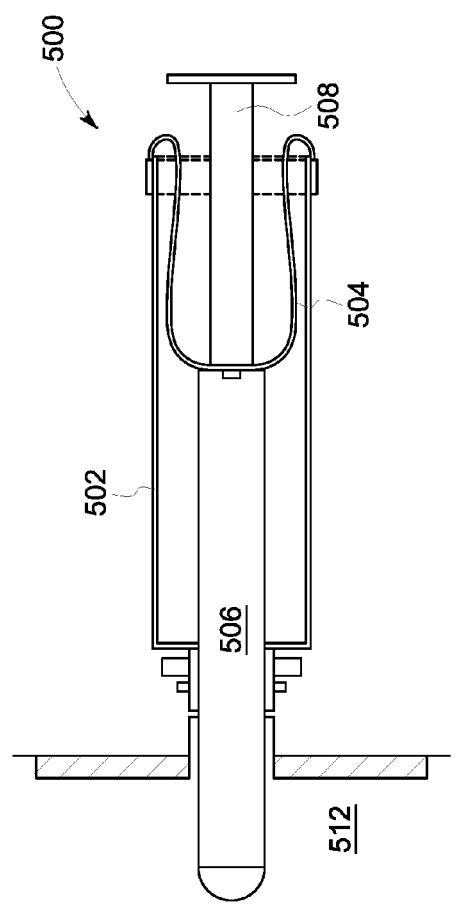
FIG. 3A
FIG. 3B

PROBE ASSEMBLY

RELATED APPLICATIONS

This application is a filing under 35 U.S.C. 371 of international application number PCT/US2012/062345, filed Oct. 28, 2012, published on May 2, 2013 as WO 2013/063550, which claims priority under 35 U.S.C. § 119(e) to U.S. Provisional Patent Application No. 61/552, 974, filed on 28 Oct. 2011, and entitled "Probe Assembly," the teachings of which are incorporated herein by reference in its entirety.

FIELD OF INVENTION

This disclosure relates generally to bioprocessing systems and methods and, in particular, to systems and methods for inserting sensors into bioreactor vessels and tubing, including flexible or semi-rigid bags or tubing.

BACKGROUND

A variety of vessels, devices, components and unit operations are known for carrying out biochemical and/or biological processes and/or manipulating liquids and other products of such processes. Increasingly, in order to avoid the time, expense, and difficulties associated with sterilizing the vessels used in biopharmaceutical manufacturing processes, single-use or disposable bioreactor bags and single-use mixer bags are used as such vessels. For instance, biological materials (e.g., animal and plant cells) including, for example, mammalian, plant or insect cells and microbial cultures can be processed using disposable or single-use mixers and bioreactors.

The manufacturing of complex biological products such as proteins (e.g., monoclonal antibodies, peptides, hormones, and vaccine immunogens) requires, in many instances, multiple processing steps ranging from cell culture (bacteria, yeast, insect, fungi, etc.) and/or fermentation, to primary recovery, purification, and others. Conventional bioreactor-based manufacturing of biological products generally utilizes batch, or fed-batch processing through a series of unit operations with subsequent off-line laboratory analysis conducted on representative samples collected from various points of the process to ensure quality.

In order to obtain timely information regarding changing conditions within a bioreactor vessel during its operation, the use of sensor technology has been employed. With regard to use of disposable bioreactors, there are recognized difficulties in sterilely inserting a sensor into a flexible-walled bioreactor or flexible tubing that feeds or drains such vessels. Further, optical, electrical, and pH sensors, for example, positioned inside a flexible bag or tubing require an attachment means that allows for a clear signal to be communicated to or from external analytical instrumentation. Thus, there is an ongoing need for an improved sensor connector and a method for inserting a sensor into flexible disposable bioreactor bags or fluid circulating tubing.

An improved device and method for sterilely inserting a non-disposable sensor or a disposable sensor into a flexible bioreactor bag or tubing would also be beneficial for use in bioreactor-based manufacturing systems that include in-line sensing in order to provide real-time data.

Because the sensor itself can be expensive, there is an on-going need for an improved device and method for sterilely inserting a sensor into a flexible bag or tubing, a device and method that facilitate the removal of the sensor from the disposable bag or tubing without damaging the sensor. With such an improved device and method, the bag or tubing can be discarded along with the sensor, or alternatively the sensor can be removed, re-sterilized, and re-used.

SUMMARY OF THE INVENTION

In accordance with the present invention there is provided a probe assembly for inserting a disposable or non-disposable sensor into a flexible bag or a semi-rigid vessel or tubing, the assembly including a distal, preferably aseptic, connector for coupling to the vessel or tubing (e.g., via a mating aseptic connector), a probe sheath comprising at least a portion that is rigid, the probe sheath extending longitudinally from the aseptic connector and having at least one inner longitudinal lumen configured to receive an elongate probe body and to permit longitudinal movement of the probe body within the probe sheath lumen, and an actuator for deploying a probe within the vessel or tubing by advancing the probe body through the aseptic connector to a position where the probe can measure at least one parameter within the vessel or tubing. In one embodiment of the invention, the entire probe sheath is rigid.

In one embodiment of the invention, the probe sheath comprises at least a portion that is non-collapsible and the inner longitudinal lumen is configured to sealably receive an elongate probe body and to permit longitudinal movement of the probe body within the probe sheath lumen.

Methods of aseptically inserting a probe into a flexible or semi-rigid vessel or tubing are also disclosed. Such methods can include the steps of (1) providing a probe assembly having a distal aseptic connector and a probe sheath extending longitudinally from the aseptic connector and having at least one inner longitudinal lumen configured to receive an elongate probe body, (2) connecting the probe assembly to a port associated with the vessel or tubing (e.g. via a mating disposable aseptic connector) and (3) inserting an elongate probe through a lumen in the probe sheath and advancing the probe through the lumen until at least a sensing portion of the elongate probe is aseptically disposed within the vessel or tubing (or otherwise in a position where the probe can measure at least one parameter within the vessel or tubing).

Another embodiment of the invention is a method of forming a probe insertion device and inserting it into a flexible-walled container or a tubing system, the method including: partially inserting a probe body into a first end of a first flexible tubing section; attaching a first end of a second flexible tubing section to a tubing port of the flexible-walled container or the tubing system; welding a second end of the first flexible tubing section to the second end of the second flexible tubing section, thereby forming a welded flexible tubing; and advancing the probe body through the welded flexible tubing and partially into the flexible-walled container or the tubing system, while allowing the first flexible tubing section of the welded flexible tubing to fold back upon itself, thereby forming a probe insertion device and inserting it into a flexible-walled container or tubing system.

BRIEF DESCRIPTION OF THE DRAWINGS

The foregoing and other objects, features and advantages of the invention will be apparent from the following more particular description of illustrative embodiments of the invention, as illustrated in the accompanying drawings in which like reference characters refer to the same parts throughout the different views. The drawings are not necessarily to scale, emphasis instead being placed upon illustrating the principles of the invention. Those skilled in the art will understand that the devices and methods specifically described herein and illustrated in the accompanying drawings are non-limiting exemplary embodiments. The features illustrated or described in connection with one exemplary embodiment can be combined with the features of other embodiments. Such modifications and variations are intended to be included within the scope of the present invention.

FIG. 1A is an cross-sectional side view of an exemplary, plunger-type probe assembly according to the invention in a detached position prior to coupling with a bag or tubing.

FIG. 1B is another cross-sectional side view of the probe assembly of FIG. 1A in a coupled position, joined to a bag or tubing.

FIG. 3A is a cross-sectional side view of yet another embodiment of a probe assembly according to the invention (with a balloon element) in an attached position but prior to probe insertion into a bag or tubing.

FIG. 3B is a cross-sectional side view of the probe assembly of FIG. 3A in a coupled position with the probe inserted into the bag or tubing.

DETAILED DESCRIPTION

Figure 1C:
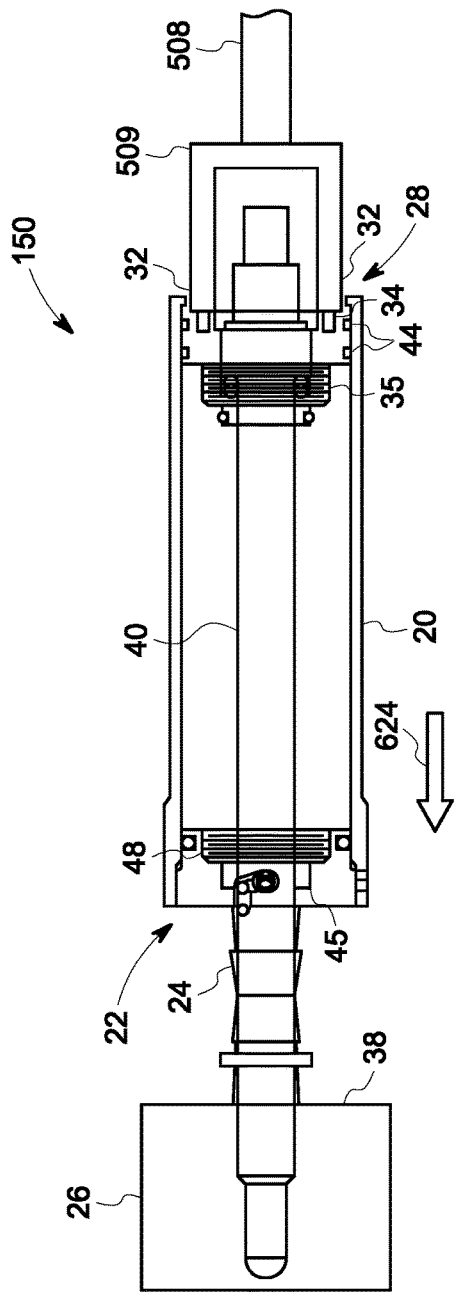
FIG. 1C is a cross-sectional side view of the probe assembly of another embodiment according to the invention of a plunger-type probe assembly in a detached position prior to coupling with a bag or tubing, wherein the probe body includes a connector plug.

As used herein, the terms "comprises," "comprising," "includes," "including," "has," "having," or any other variation thereof, are intended to cover a non-exclusive inclusion. For example, a process, article, or apparatus that comprises a list of elements is not necessarily limited to only those elements but may include other elements not expressly listed or inherent to such process, article, or apparatus. Further, unless expressly stated to the contrary, "or" refers to an inclusive or and not to an exclusive "or."

Additionally, any examples or illustrations given herein are not to be regarded in any way as restrictions on, limits to, or express definitions of, any term or terms with which they are utilized. Instead, these examples or illustrations are to be regarded as being described with respect to one particular embodiment and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to: "for example," "for instance," "e.g.," and "in one embodiment."

The term "flexible," as used herein, refers to a structure or material that is pliable, or capable of being bent without breaking, and may also refer to a material that is compressible or expandable. An example of a flexible structure is a bag formed of polyethylene film. The terms "rigid" and "semi-rigid" are used herein interchangeably to describe structures that are "non-collapsible," that is to say structures that do not fold, collapse, or otherwise deform under normal forces to substantially reduce their elongate dimension. "Collapsible" is defined to include substantially flexible material that will fold onto or into itself, such as, for example, fabrics and materials that form "accordion-like" structures in response to a compressive force. Depending on the context, "semi-rigid" can also denote a structure that is more flexible than a "rigid" element, e.g., a bendable tube or conduit, but still one that does not collapse longitudinally under normal conditions and forces.

A "vessel" as the term is used herein, means a flexible bag, a flexible container, a semi-rigid container, or a flexible or semi-rigid tubing, as the case may be. The term "vessel" as used herein is intended to encompass bioreactor vessels having a wall or a portion of a wall that is flexible or semi-rigid, single use flexible bags, as well as other containers or conduits commonly used in biological or biochemical processing, including, for example, cell culture/purification systems, mixing systems, media/buffer preparation systems, and filtration/purification systems, e.g., chromatography and tangential flow filter systems, and their associated flow paths. As used herein, the term "bag" means a flexible or semi-rigid container, vessel, or tubing.

Typically a flexible bag used for mixing or bioprocessing is supported by a rigid support structure or supported within a rigid vessel. A probe assembly according to an embodiment of the invention is particularly useful for attaching to a disposable or single use flexible bioreactor or mixer bag, or a flexible tubing. Sterilizing a probe before it is inserted into a reactor bag or vessel is often essential. When the probe is inserted via a probe assembly, it may be necessary to sterilize the entire probe assembly, including any sheaths, connectors, and tubes, as well as the probe itself, prior to inserting the probe into the reactor vessel. Common methods of sterilization include, but are not limited to, autoclaving, radiation treatment, and chemical treatment. When an autoclave is used, it can be important for steam to reach all of the interior surfaces of a probe assembly, as well as the exterior portions.

A typical industry standard size sensor is about 12 mm diameter×225 mm long, but any size sensor can be used. The sensor can be installed as an elongate probe body that is configured to be advanced into the vessel via a probe sheath.

This particularly advantageous when the vessel has a flexible or non-rigid form. An aseptic connector is commonly used to perform the sterile connection between the probe sheath assembly and the sterile vessel.

Aseptic connectors typically are two-part constructions (either a male and matching female part or a pair of "genderless" parts) that are joined together. One part of the aseptic connect can be joined to the vessel, e.g., by a suitable sized length of tubing. This aseptic connector is then coupled to a corresponding aseptic connector part on the probe assembly, as described below. When the aseptic connector that is mounted on the container is connected to the aseptic connector on the sterilized probe sheath assembly, a sterile passageway is formed between the container and the probe sheath, a passageway through which a sterile sensor or probe can be inserted such that it can take measurements of conditions inside the vessel.

Plunger-Type Assembly

Turning now to FIG. 1A, a plunger-type probe assembly 100 is shown having a hollow probe sheath 20 which has a barbed tube fitting 24 at a first end 22 which is used to connect the probe sheath 20 to a disposable aseptic connector 26, and the second end 28 of the probe sheath 20 provides an opening 32 into which a sensor or probe body 40 and plunger 34 is inserted. The disposable aseptic connector 26 is attached using a suitably sized section of tubing 36 to the barbed tube fitting 24 on the first end 22 of the probe sheath 20, thereby forming a closure 38 at that distal end capable of maintaining a sterile seal. At the left, bag wall 64 has a port 72 formed in the exterior of the bag 512. Port 72 may have a hose barb plate 70 welded to the inside of the bag wall 64, and a valve protrusion, such as a hose barb 74, projecting from the bag 512.

The probe sheath plunger 34 has an opening 33 into which the sensor or probe body 40 can be inserted and secured such that a seal capable of being sterilized is formed between the sensor or probe body 40 and the probe sheath plunger 34. The probe sheath plunger 34 is positioned inside the opening 32 of the probe sheath 20 such that the sensor/ probe body 40 with the sensing element can pass through the inside 42 of the probe sheath 20 and reach to the barbed fitting 24 on the first end 22 of the probe sheath 20.

As shown in FIG. 1B, a seal 44 exists between the inside 42 of the probe sheath 20 and the outside 35 of the probe sheath plunger 34 which allows relative movement between the probe sheath 20 and the probe sheath plunger 34. The plunger 34 can be a manual plunger or a low-rpm, high-torque motor assembly 31. The seal 44 between the probe sheath 20 and the probe sheath plunger 34 is configured so that the seal 44 will provide a sterile barrier between the volume 42 inside the probe sheath 20 and the outside of the probe sheath 20 when the probe sheath 20 is sterilized.

The probe sheath plunger 34 can be moved relative to the probe sheath 20 so that when the sensor or probe body 40 needs to be inserted through the wall 64 of a flexible or semi-rigid container, column, or tubing, the plunger 34 is moved such that it decreases the internal volume 42 inside the probe sheath 20, and the sensor or probe body 40 then moves down the sheath to the disposable aseptic connector 26.

As shown in FIG. 1B, the probe assembly 100 can further include a locking mechanism such as a threaded portion 48, which portion 48 can include a catch, detent, for example, positioned to maintain the probe sheath plunger 34 in the fully compressed position, as shown in FIG. 1B, when the sensor or probe body 40 is through the wall 64 of the flexible or semi-rigid container or tubing. Arrow 60 shows direction of movement of the elongate probe body 40 longitudinally in the direction of the bag 512.

The bag 512 can have an entry point or port 72 formed in the exterior of the bag 512. This port 72 can include a hose barb plate 70 welded to the inside of the bag wall 64 and a valve protrusion, such as hose barb 74 projecting from the bag 512. The valve protrusion 74 may be integrally formed in the exterior of the bag 512, for example by welding a hose barb 74 into the bag film 64 in a disposable bag type reactor. The valve protrusion 74 should releasably engage an aseptic connector 76, such that the aseptic connector can mate with another portion of an aseptic connector 26. The aseptic connector 76 can be connected in any suitable manner to protrusion 74, so long as the connection does not leak. FIG. 1B depicts a disposable aseptic connector part 76 mating with a hose barb 74 secured by a clamping mechanism 78, such as a tri-clover type clamp.

The aseptic connector can include two separate portions, or parts 26, 76. These portions can mate together in a traditional male and female relationship, as is shown in FIG. 1A. Other types of connectors may be used with the disclosed probe assembly. For example, the aseptic connector portions can connect to one-another in a non-mating fashion, such that each portion of the aseptic connector is identical. Clamping mechanisms can be utilized to ensure proper sealing and non-leaking function of the aseptic connector. The aseptic connector can include a non-permeable membrane sealing the connectors portions from contamination from the ambient environment, this membrane being designed to be removed prior to insertion of the probe body through the aseptic connector. The aseptic connector can be appropriately sized to match the diameter of a desired probe, vessel port, probe assembly connection size, or any other desired sizing variable. The type of aseptic connector can be selected without regard to the embodiment of the probe sheath type. Aseptic connectors are available from various commercial sources, such as Colder Products, Pall, Millipore and GE Healthcare.

The probe sheath plunger 34 can be disposed within the probe sheath 20 such that no ambient air, liquids, or other matter from the exterior of sheath 20 can pass to the sheath interior 42. The probe sheath plunger 34 can be formed of a rubber material such that the plunger can slide along the probe sheath 20 and such that the plunger 34 forms a seal directly against the probe sheath 20. Alternatively, as explained above the assembly can include seals 44. Alternatively, in another embodiment there is no plunger 34; instead, for example, a portion of the probe body serves as the actuator. In this case, the seals 44 contact the elongate probe body directly, aseptically sealing the interior 42 from the ambient environment.

FIG. 1C depicts another embodiment of the disclosed probe assembly wherein the probe sheath includes at least two parts, one of which comprises a tubular section of the probe sheath which can be removed after the probe sheath has been collapsed and the probe body is locked together with a bag port.

The embodiment in FIG. 1C includes a plunger-type probe assembly 150 having a hollow probe sheath 20 having an inside wall, a first end 22, and a second end 28 into which a rear plunger 34 has been inserted through opening 32. Rear plunger 34 is secured to the inside wall of probe sheath 20, for example by means of a bayonette fitting with prongs 62 (shown in FIG. 1D but not shown in FIG. 1C). The front portion of rear plunger 34 includes threads 35 arranged for mating and connecting to a threaded portion 48 of a connector plug 45 in the front portion of the probe sheath 20. A sensor or probe body 40 is axially positioned within probe sheath 20 and secured at its rear end within rear plunger 34, and secured at its front end within connector plug 45. The front portion of sensor or probe body 40 is positioned in a disposable aseptic connector 26 which is attached, for example, using a suitably sized section of tubing to the barbed tube fitting 24 on the first end 22 of the probe sheath 20, thereby forming a closure capable of maintaining a sterile seal. A detachable tool 509 to which is affixed handle 508 is connected to the probe sheath 20. The seals 44 between the probe sheath 20 and the probe sheath plunger 34 are configured so that the seal 44 will provide a sterile barrier between the inside of the probe sheath 20 and the outside of the probe sheath 20 when the probe sheath 20 is sterilized. Seals 44 can be O-rings.

Figure 1D:
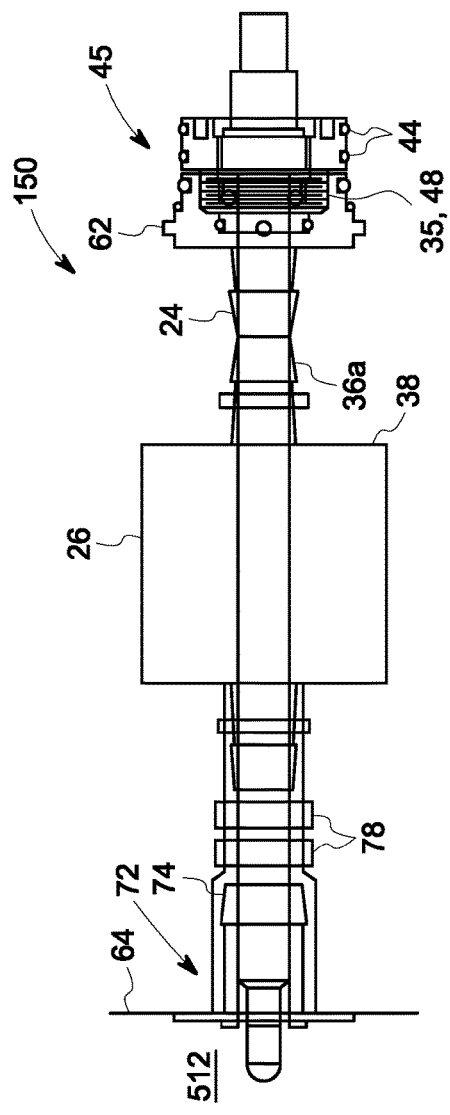
FIG. 1D is a cross-sectional side view of the probe assembly shown in FIG. 1C, wherein the probe assembly is in a coupled position, joined to a bag or tubing.

Arrow 624 shows the direction in which the rear plunger 34 is moved to advance the probe body 40 into the bag 512 as shown in FIG. 1D.

FIG. 1D shows the plunger-type probe assembly 150 in a collapsed position from the position that is depicted in FIG. 1C. At the left, bag wall 64 of container 512 has a port 72 formed in the exterior of the bag 512. Port 72 may have a hose barb plate welded to the inside of the bag wall 64, and a valve protrusion, such as a hose barb 74, projecting from the bag wall 64. The sensor/ probe body 40 with the sensing element has advanced, passing through the inside of the probe sheath 20, and through the disposable aseptic connector 26 with end wall 38, and through the bag wall 64 to the interior of bag 512. Clamping mechanisms 78 secure the probe body 40.

FIG. 1D also shows a connection port 36a of the disposable aseptic connector 26 connected to the barbed tube fitting 24 of the probe sheath 20. The threaded portion 35 of probe sheath plunger 34 is shown mated with the threaded portion 48 of connector plug 45. The tubular portion of probe sheath 20 has been removed, along with tool 509 with handle 508, the tool having being used to detach the probe sheath 20. The connector plug 45 is shown with the prongs 62 that had been used to attach the rear plunger 34 to the inside wall of probe sheath 20.

Telescoping Assembly

Figure 2A:
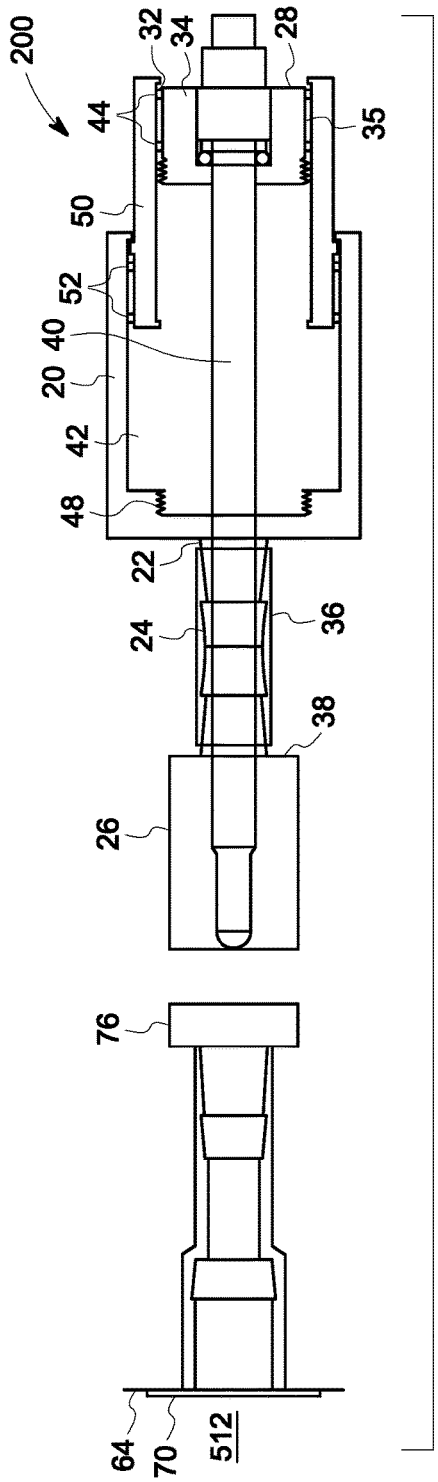
FIG. 2A is a cross-sectional side view of another embodiment of a probe assembly according to the invention (with telescoping elements) in a detached position prior to coupling with a bag or tubing.
Figure 2B:
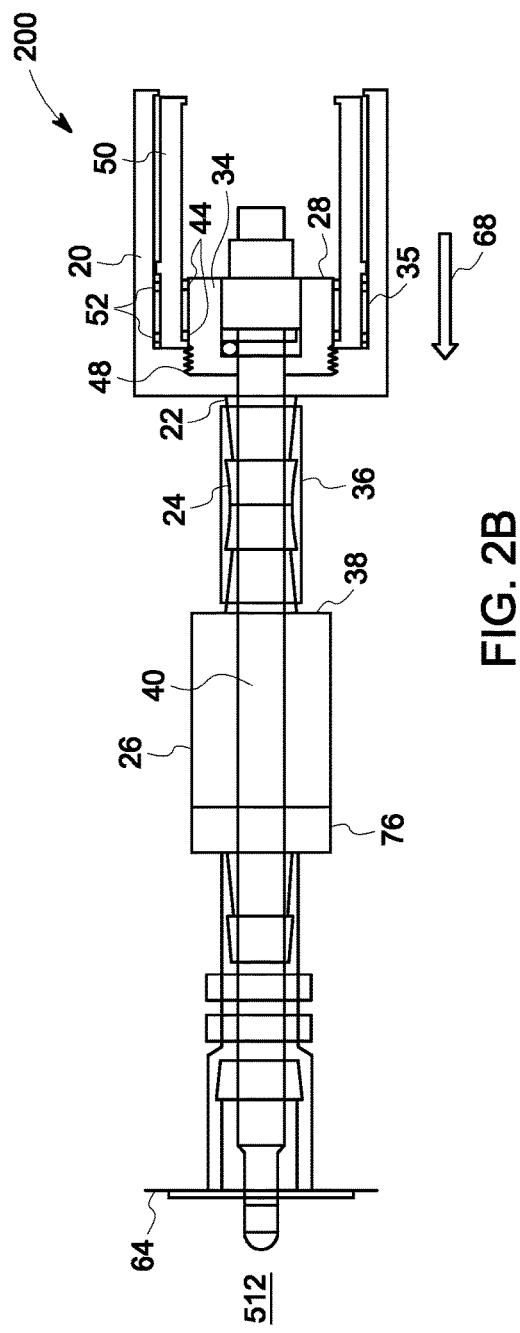
FIG. 2B is a cross-sectional side view of the probe assembly of FIG. 2A in a coupled position, joined to the bag or tubing.

FIG. 2A is a side elevation, partially cutaway view of a telescoping plunger probe assembly 200 according to another embodiment of the invention. The telescoping assembly 200 differs from the above description only in that the probe sheath 20 may consist of one or more sections 50 that allow the sections of the probe sheath 20 to be telescoped into one another, such that the overall length of the probe sheath 20 is reduced when the plunger 34 is fully compressed into the probe sheath 20, as shown in FIG. 2B. Arrow 68 shows direction of movement of the elongate probe body 40 longitudinally in the direction of the bag wall 64. The telescoping sections 50 are configured to provide moveable seals 52 between the sections 50, and these seals 52 are such that they, along with the other seals 44 described above can provide a sterile interior space 42 formed inside the probe sheath 20 once the assembly has been sterilized.

As discussed above, the probe sheath assembly can again include a locking mechanism, such as a threaded potion 48, a catch, detent, etc., to maintain the telescoping sections 50 or segments of the probe sheath 20 in their fully compressed configuration as shown in FIG. 2B, or telescoped configuration when the probe sheath plunger 34 is in the fully compressed position and the sensor or probe is inserted into the flexible or semi-rigid container or tubing 64.

Balloon Plunger Type Assembly

FIGS. 3A and 3B are side elevation, partially cutaway views of a balloon plunger-type probe assembly 500 according to another embodiment of the invention, wherein a rigid or semi-rigid sheath 502 is connected to a flexible sheath portion 504. The flexible sheath portion 504 can be connected to an elongate sensor or probe body 506 or to an elongate probe handle 508 that is attached to the elongate probe body 506 disposed within the probe sheath 502, 504.

The flexible portion 504 can be fixed to the rigid or semi-rigid sheath portion 502 with means known in the art, such as clamp 510. The flexible portion 504 can be elastic, or inelastic, so long as it is deformable and is able to maintain a seal with sheath 502 when the probe body 506 or handle 508 is moved longitudinally in the direction of the bag 512. When the probe 506 is disposed within the bag 512, the flexible portion 504 can be disposed within the rigid or semi-rigid portion 502, as shown in FIG. 3B.

The sensor used in a probe sheath 20 according to an embodiment of the invention can be any type of sensor. Non-limiting examples include conductivity, pH, dissolved oxygen, and turbidity sensors.

The probe sheath 20 according to an embodiment of the present invention facilitates the removal or retraction of a sensor from a flexible or semi-rigid container 64 or a flexible or semi-rigid tubing 64 so that the sensor can be sterilized and re-used in another device.

Probe Insertion Device Not Requiring A Gas-Permeable Membrane Connector

At the outset, this invention of the invention is described in its broadest overall aspects, with a more detailed description following.

A probe insertion device that does not require a gas permeable membrane connector is described. The probe insertion device 700b, FIG. 5B, according to an embodiment of the invention includes a thin-walled collapsible tubing 604a 605b that can be folded in upon itself, as shown FIGS. 5B, 5C, and 5D.

Figure 4A:
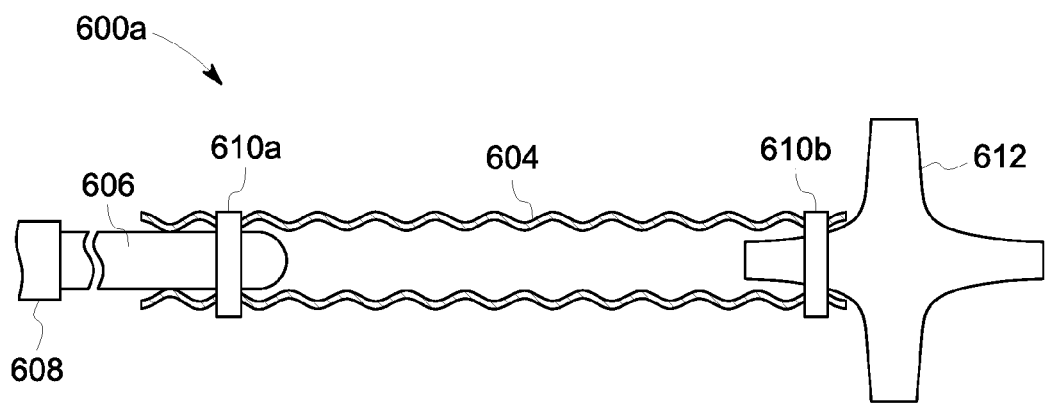
FIG. 4A is a cross-sectional side view of yet another embodiment of an aseptic connector device according to the invention in a position that is prior to welding a section (Part "i") thereof to a section (Part "ii") of the tubing that is shown in FIG. 4B, the tubing attached to a flexible walled container or tubing.

One embodiment of a method of producing the disclosed probe insertion device is depicted in FIGS. 4A through 5D. FIG. 4A depicts a first starting component 600a including a disposable or non-disposable probe body 606 having an elongate probe handle 608 and which is partially inserted into a first end of a section of flexible tubing 604 and clamped in place by clamp 610a. The section of autoclavable or irradiatable, weldable, thin-walled, flexible tubing 604 is of sufficient length to fit in a standard tubing welder. The second end of flexible tubing 604 is clamped by clamp 610b to a sterile, autoclavable, gas vent filter 612 having an open end partially inserted into the flexible tubing 604. Filter 612 may be, for example, a 0.2 micron filter.

Figure 4B:
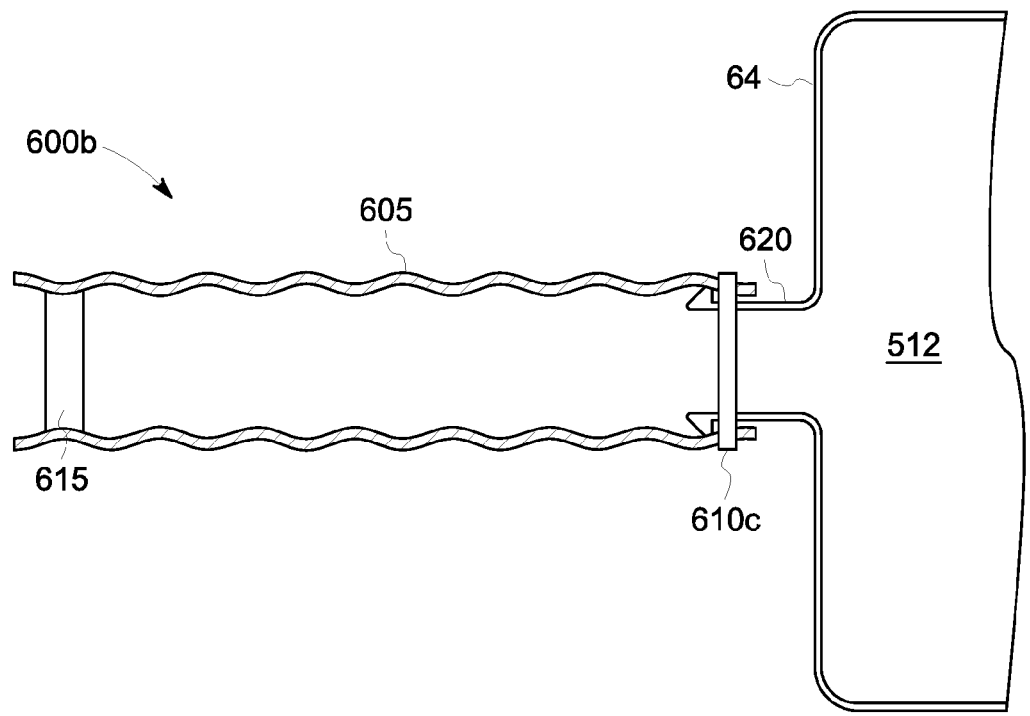

FIG. 4B depicts a second starting component 600b comprising a section of flexible tubing 605 having a plug 615 or welded closing at a first end. Flexible tubing 605, in one embodiment of the invention, has a wall that is thicker than the wall of tubing 604. The section of flexible tubing 605 is autoclavable or irradiatable and weldable and of sufficient length to fit in a standard tubing welder. Tubing 605 is clamped by clamp 610c or otherwise attached to a container tubing port 620 secured to wall 64 of flexible container 512 or to a tubing system. The flexible container 512 or tubing system has preferably been irradiated, autoclaved or otherwise sterilized.

Figure 5A:
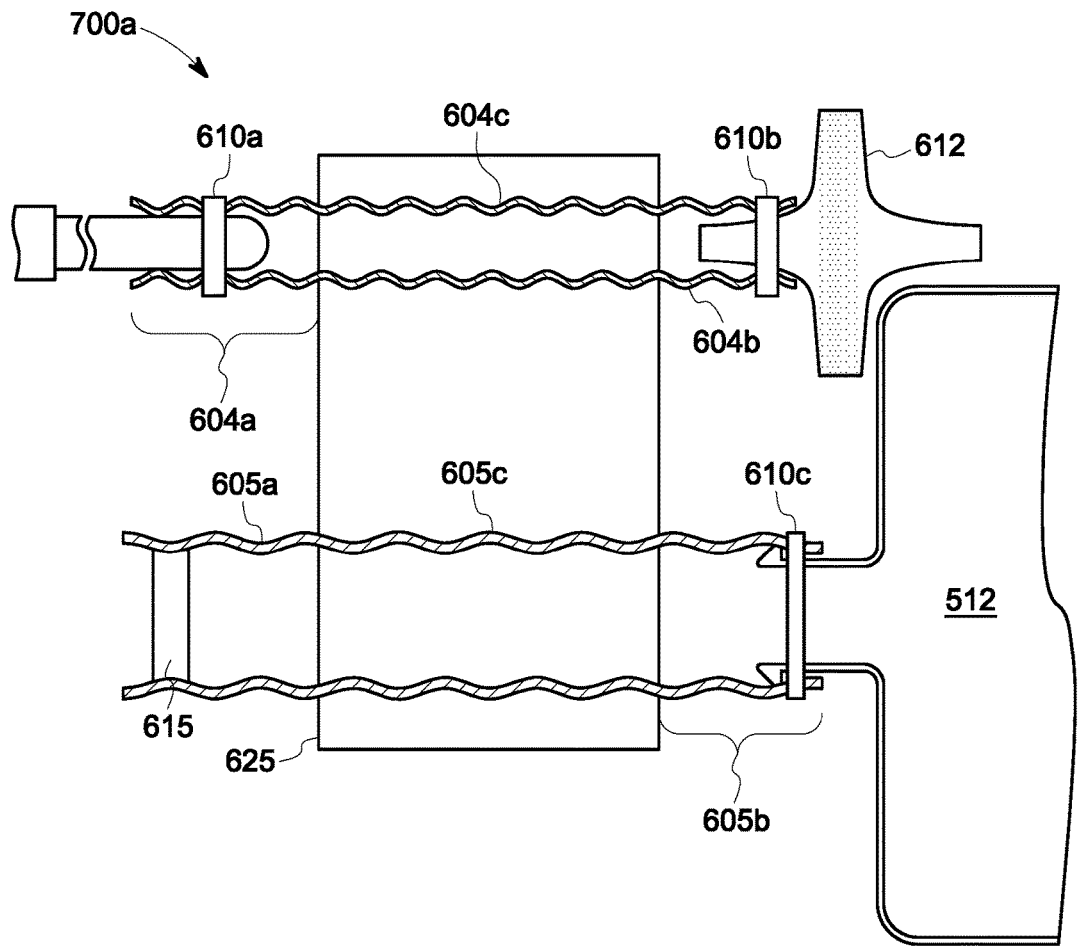
FIG. 5A shows a cross-sectional side view of the aseptic connector device of FIG. 4A and the tubing shown in FIG. 4B positioned within a tubing welder.
Figure 5B:
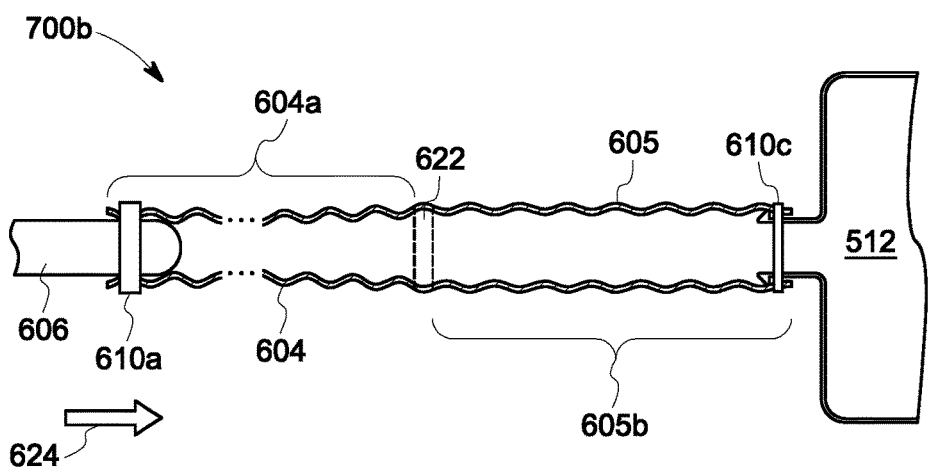
FIG. 5B shows Part "i" of the aseptic connector device and Part "ii" of the tubing welded together to form a probe assembly according to an embodiment of the invention.

The first and second starting components 600a and 600b, respectively, are autoclaved, irradiated, or otherwise sterilized. The middle sections of the starting components are then placed in a standard tubing welder 625. FIG. 5A depicts an arrangement, 700a wherein a middle section of each of the first starting component 600a and the second starting component 600b are positioned within a standard tubing welder 625. Part i, 604a and Part ii, 605b are welded together at weld joint 622 as shown in FIG. 5B. The filter 612 of the first starting component 600a and the plugged tubing end of the second starting component 600b are discarded.

Figure 5C:
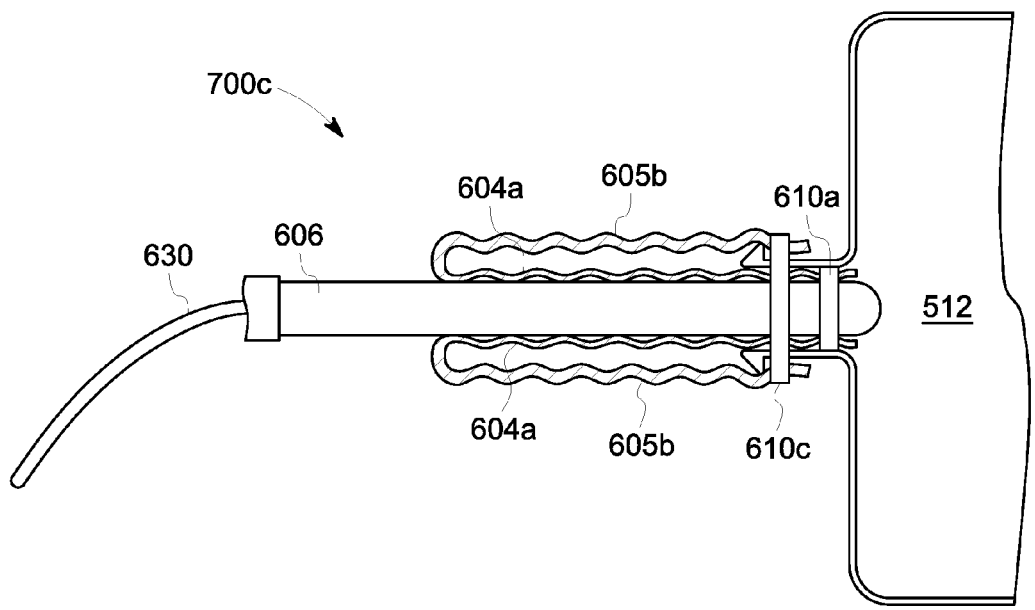
FIG. 5C shows the probe assembly with the probe body in a position after it has been pushed into the container or tubing system according to an embodiment of the invention.

As shown in FIG. 5B, the probe insertion device 700b in FIG. 5B has been formed from two flexible tubing parts, Part i and Part ii, 604a and 605b, respectively, which have been autoclaved, irradiated, or otherwise sterilized along with a sacrificial gas permeable vent filter 612 that is discarded after the parts 604a and 605b are placed in a tube welder 625 and welded together. As also shown in FIG. 4B, FIG. 5A and 5B, flexible tubing 605 and/ or Part ii, 605b is clamped by clamp 601c or otherwise attached and fluidically connected to container tubing port 620 of flexible or semi-rigid container 512 or to a flexible tubing into which the probe 606 is to be inserted. After Parts i and ii, 604a and 605b respectively have been welded together as shown in FIG. 5B, the probe body 606 is advanced in the direction of arrow 624 and inserted into the container 512 by collapsing the flexible tubing 604, 604a inward as the probe is pushed or otherwise advanced through the weld 622, through tubing 605, 605b and through the container tubing port 620 and into the container 512. FIG. 5C shows the resulting probe assembly 700c.

Figure 5D:
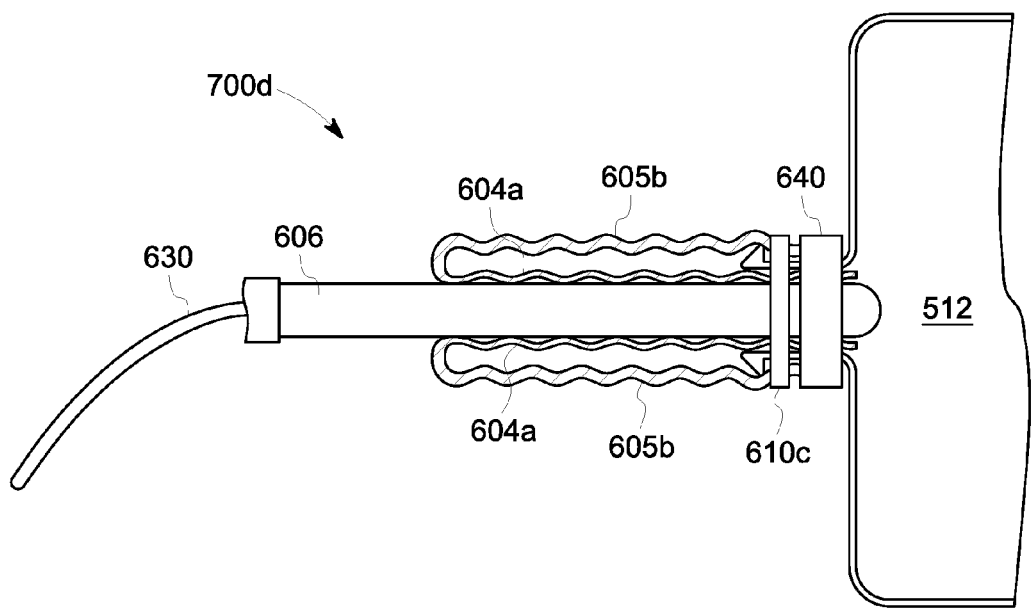
FIG. 5D shows the system of FIG. 5C including an outer, perimeter hose clamp securing the probe in position.

FIG. 5C shows that the flexible tubing Part i, 604a has folded back on itself, and is now positioned inside of flexible tubing Part ii, 605b. Probe body 606 with attached probe wire 630 is shown as positioned or "sandwiched" between two surfaces formed of tubing 604a. As shown in FIG. 5D, a perimeter or outer hose clamp 640 can be attached to secure the probe body 606 in position and to prevent backward leaking.

EQUIVALENTS

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A probe assembly for inserting a probe into a flexible or semi-rigid vessel or tubing, the assembly comprising:
   a distal aseptic connector for coupling to the vessel or tubing;
   a probe sheath comprising at least a portion that is rigid, the probe sheath extending longitudinally from the aseptic connector and having at least one inner longitudinal volume configured to receive an elongate probe body and to permit longitudinal movement of the probe body within the probe sheath;
   an actuator for deploying a probe within the vessel or tubing by advancing the probe body through the aseptic connector to a position sufficient for the probe to measure at least one parameter within the vessel or tubing; and
   wherein the distal aseptic connector has a tube section that connects to a barbed fitting of the probe sheath.

2. The probe assembly of claim 1, wherein the distal aseptic connector is further adapted to couple to a mating aseptic connector associated with the vessel or tubing.

3. The probe assembly of claim 1, wherein the probe sheath is non collapsible and the actuator moves the probe body longitudinally within the sheath.

4. The probe assembly of claim 1, wherein the probe sheath comprises at least two concentric rigid sheath elements and the actuator moves the probe body longitudinally within the sheath by telescoping one sheath element within another sheath element.

5. The probe assembly of claim 1, wherein the actuator comprises a motor assembly.

6. The probe assembly of claim 1, wherein the probe assembly is configured to be sterilized.

7. The probe assembly of claim 1, wherein the aseptic connector is joined to the probe sheath by a section of flexible tubing.

8. The probe assembly of claim 1, wherein the probe assembly further comprises a probe sheath plunger configured to sealably engage the probe sheath and the elongate probe body.

9. The probe assembly of claim 8, wherein the probe sheath plunger is further adapted to move longitudinally within the inner longitudinal volume.

10. The probe assembly of claim 1, wherein the probe sheath further comprises at least one catch on an end of the at least one inner longitudinal volume configured to fix the position of the probe body in a longitudinal direction.

11. A method of aseptically inserting a probe into a flexible or semi-rigid vessel or tubing, the method comprising:
    providing a probe assembly having an elongate probe disposed within an inner longitudinal volume of a non-collapsible probe sheath and an aseptic connector joined to the probe sheath;
    connecting the probe assembly to a port in the vessel or tubing via the aseptic connector;
    advancing the probe through the inner longitudinal volume and the aseptic connector such that a sensing portion of the elongate probe is aseptically disposed within the vessel or tubing; and
    wherein the aseptic connector has a tube section that connects to a barbed fitting of the probe sheath.

12. The method of claim 11, wherein the step of connecting the probe assembly to the vessel or tubing further comprises coupling the aseptic connector of the probe assembly to a mating aseptic connector associated with the vessel or tubing.

13. The method of claim 11, wherein the step of advancing the probe through the inner longitudinal volume and the aseptic connector further comprises actuating longitudinal movement of the elongate probe with a mechanical device.

* * * * *